United States Patent [19]

Kühle et al.

[11] 4,427,698

[45] Jan. 24, 1984

[54] USE OF N,N-DIMETHYL-N'-P-TOLYL-N'-DICHLOROFLUOROMETHYLTHIO-SULPHAMIDE FOR COMBATING FUNGI WHICH DAMAGE WOOD

[75] Inventors: Engelbert Kühle, Bergisch-Gladbach; Wilfried Paulus, Krefeld; Erich Klauke, Odenthal; Hermann Genth, Krefeld, all of Fed. Rep. of Germany

[73] Assignee: Bayer Aktiengesellschaft, Leverkusen, Fed. Rep. of Germany

[21] Appl. No.: 330,983

[22] Filed: Dec. 15, 1981

Related U.S. Application Data

[63] Continuation of Ser. No. 83,504, Oct. 10, 1979, abandoned.

[30] Foreign Application Priority Data

Oct. 13, 1978 [DE] Fed. Rep. of Germany ....... 2844605

[51] Int. Cl.$^3$ ............................................. A61K 31/18
[52] U.S. Cl. ..................................................... 424/321
[58] Field of Search .......................................... 424/321

[56] References Cited

U.S. PATENT DOCUMENTS 3,285,929 11/1966 Klauke et al. ....................... 260/301
3,499,030 3/1970 Kuhle et al. ..................... 260/551 S

FOREIGN PATENT DOCUMENTS 1056642 1/1967 United Kingdom .

*Primary Examiner*—Stanley J. Friedman
*Attorney, Agent, or Firm*—Sprung, Horn, Kramer & Woods

[57] ABSTRACT

N,N-dimethyl-N'-p-tolyl-N'-dichlorofluoromethylthio-sulphamide and its use as an anti-fungal agent especially in preventing fungi damage to wood.

9 Claims, No Drawings

USE OF N,N-DIMETHYL-N'-P-TOLYL-N'-DICHLOROFLUOROMETHYLTHIO-SULPHAMIDE FOR COMBATING FUNGI WHICH DAMAGE WOOD

This is a continuation of application Ser. No. 083,504 filed Oct. 10, 1979 now abandoned.

The invention relates to the use of N,N-dimethyl-N'-p-tolyl-N'-dichlorofluoromethylthio-sulphamide for combating fungi which damage wood.

Sulphamides such as N,N-dimethyl-N'-tolyl-N'-dichlorofluoromethylthio-sulphamide are known from German Patent Specification No. 1,238,139 as agents against the attack of paints and plastics coatings by moulds and bacteria. The microbicidal agents are incorporated in the paints or in the plastic.

When providing wood with a microbicidal finish it is generally not possible to incorporate a solid active compound into the wood. It is therefore generally customary to formulate the active compound with a solvent and to apply the formulation to the wood (Chemie der Pflanzenschutzund Schädlingsbekämpfungsmittel (Chemistry of Plant Protection Agents and Pest Control Agents), volume 4, page 257-72, Springer Verlag 1977).

The action of N,N-dimethyl-N'-phenyl-N'-(fluorodichloromethylthio)-sulphamide against fungi which damage wood is described in "Holz als Roh-und Werkstoff 35, (1977) 233–237". However, N,N-dimethyl-N'-phenyl-N'-(fluorodichloromethylthio)-sulphamide has very poor solubility in the formulating agents customary for wood protection agents, so that large amounts of formulating agent are required in order to bring the requisite amount of active compound onto and/or into the wood.

The use of N,N-dimethyl-N'-p-tolyl-N'-dichlorofluoromethylthio-sulphamide in wood impregnating agents has been found.

N,N-Dimethyl-N'-p-tolyl-N'-dichlorofluoromethylthio-sulphamide is a new agent for combating fungi which damage wood and surprisingly it is very readily soluble in organic solvents, so that it is possible to use it as an active compound in wood impregnating agents without difficulty and with advantages.

Solvents which may be mentioned for the active compound according to the invention are the solvents customarily used in wood impregnating agents (Ullmann, volume 8, page 553, 1957).

Examples which may be mentioned are: petroleum fractions and benzene fractions, such as petroleum spirits, and also solubilizing agents, such as ethyl acetate and xylene. Preferred solvents are mixtures of aromatic hydrocarbons, whose boiling point is between 150° and 180° C. and benzene fractions, whose boiling point is between 140° and 200° C.

In general, the active compound according to the invention is dissolved in amounts of 0.35 to 3.5% and preferably of 1.5 to 3% in the solvent.

The result of the unexpectedly good solubility of the active compound according to the invention in the solvents customarily used for wood impregnating agents is that the requisite volume for application is low. Because of this, the low toxicity of the active compound according to the invention is particularly important. In contrast to known active compounds which are used or proposed for combating fungi which damage wood, for example pentachlorophenol, the active compound according to the invention has neither a cumulative nor a percutaneous toxic action.

The preparation of N,N-dimethyl-N'-p-tolyl-N'-dichlorofluoromethylthio-sulphamide is known (French Patent No. 1,310,083) and can be effected, for example, by reacting N,N-dimethyl-N'-p-tolyl-sulphamide with fluorodichloromethanesulphenyl chloride.

N,N-Dimethyl-N'-p-tolyl-N'-dichlorofluoromethylthio-sulphamide is active against wood-damaging fungi such as *Ceratocystis piceae, Ceratocystis pini, Ceratocystis coerulenceus, Chaetomium globosum, Coniophora cerebella, Coriolus versicolor, Lentinus tigrinus* and *Poria vaporaria*.

The active compound according to the invention is formulated in the customary manner, for example by stirring the active compound into the formulating agent.

Of course, it is possible to combine the active compound according to the invention with other active compounds. Combinations with benzimidazolyl methylcarbamates, thiazolylbenzimidazole, zinc dimethyldithiocarbamate, tetramethylthiuram disulphide, N-nitroso-cyclohexyl-hydroxylamine and N-cyclohexyl-N-methoxy-2,5-dimethyl-3-furamide are preferred.

EXAMPLE 1

Determination of the minimum inhibitory concentration (MIC)

The active compound according to the invention is added, in concentrations of 2 mg/l to 5,000 mg/l, to an agar which is prepared from beer wort and peptone. After the agar has solidified, it is contaminated with pure cultures of the test organisms listed in Table 1. After storing for 2 weeks at 28° C. and 60–70% relative atmospheric humidity the MIC is determined. MIC is the lowest concentration of active compound with which no growth due to the type of microbes used takes place; it is indicated in Table 1 below:

TABLE 1

Listing of the MIC values in mg/l for the action of the active compound indicated below on fungi:

| Test organisms | N,N—Dimethyl-N'—p-tolyl-N'—dichlorofluoromethylthio-sulphamide |
|---|---|
| *Ceratocystis pini* | 20 |
| *Ceratocystis coerulenceus,* | 20 |
| *Coniophora cerebella* | 10 |
| *Chaetomium globosum* | 10 |
| *Lentinus tigrinus* | 5 |
| *Poria Vaporaria* | 2 |

EXAMPLE 2

Solubilities in % by weight of N,N-dimethyl-N'-p-tolyl-N'-dichlorofluoromethylthio-sulphamide (A) compared with N,N-dimethyl-N'-phenyl-N'-dichlorofluoromethylthio-sulphamide (B) and N-dichlorofluoromethylthio-phthalimide (C).

TABLE 2

| | Solubilities in % by weight | | |
|---|---|---|---|
| | Active compound | | |
| Solvent | A | B | C |
| Ethyl acetate | 33 | 11 | 8 |
| Methanol | 5 | 1.5 | 1.2 |
| Mixture of aromatic hydrocarbons, boiling point 159–175° C. | 20 | 7.5 | 4.2 |
| Benzine fraction, | 2.5 | 1.2 | 0.3 |

TABLE 2-continued

| Solvent | Solubilities in % by weight |  |  |
|---|---|---|---|
|  | Active compound |  |  |
|  | A | B | C |
| boiling point 140–190° C. Xylene | 29 | 6.5 | 3.6 |

EXAMPLE 3

Toxicological investigations with
N,N-dimethyl-N'-p-tolyl-N'-dichlorofluoromethylthio-sulphamide After a single administration by means of a probang to male rats N,N-dimethyl-N'-p-tolyl-N'-dichlorofluoromethylthio-sulphamide dissolved in acetone has an $LD_{50}$ perorally of >2,500 mg/kg of body weight. The $LD_{50}$ was calculated by means of Probit analysis (Fink et al, Methods of information in medicin 5, 19, 1966).

Comparison substance

Pentachlorophenol; $LD_{50}$ perorally 160 mg/kg of body weight in rats (Caines, Toxycology and Applied Pharmacology 14, 515 (1969)).

The cutaneous treatment of male rats with N,N-dimethyl-N'-p-tolyl-N'-dichlorofluoromethylthio-sulphamide showed that N,N-dimethyl-N'-p-tolyl-N'-dichlorofluoromethylthio-sulphamide percutaneously has just as low a toxicity as the known N,N-dimethyl-N'-phenyl-N'-dichlorofluoromethylthio-sulphamide; the $LD_{50}$ cutaneously is >500 mg/kg. Pentachlorophenol, on the other hand, percutaneously has a toxic action; $LD_{50}$ cutaneously 325 mg/kg.

What is claimed is:

1. A process for combating fungi in wood which comprised contacting said wood with 0.35 to 3.5 parts by weight of N,N-dimethyl-N'-p-tolyl-N'-dichlorofluoromethylthio-sulphamide per part by weight wood.

2. A process according to claim 1 wherein said wood contains a Basidiomycete.

3. A process according to claim 1, wherein said wood is contacted with 1.5 to 3 parts by weight of N,N-dimethyl-N'-p-tolyl-N'-dichlorofluoromethylthio-sulphamide per part by weight wood.

4. A process according to claim 1, wherein said wood contains a fungus selected from the group consisting of *Ceratocystis piceae, Cetatocystis pini, Ceratocystis coerulenceus, Chaetomium globosum, Coniophoro cerebella, Coriolus versicolor, Lentinus tigrinus* and *Poria vaporaria.*

5. A process according to claim 1, wherein said N,N-dimethyl-N'-p-tolyl-N'-dichlorofluoromethylthio-sulphamide is applied to said wood in the form f a solution where the solvent comprises a fraction, a benzene fraction, petroleum spirits, ethyl acetate or xylene.

6. A process according to claim 5, wherein said solution comprises ethyl acetate, xylene or a mixture of aromatic hydrocarbons whose boiling point is between 150° and 180° C. or a benzene fraction whose boiling point is between 140° and 200° C.

7. A process according to claim 5, wherein said N-dimethyl-N'-p-tolyl-N'-dichlorofluoromethylthio-sulphamide is employed in the form of a solution in a solvent comprising ethyl acetate, methanol, a mixture of aromatic hydrocarbons of boiling point 159°–175° C., a benzene fraction of boiling point 140°–190° C. or xylene.

8. A process according to claim 5, wherein said wood contains a fungus selected from the group consisting of *Ceratocystis piceae, Ceratocystis pini, Cetatocystis coerulenceus, Chaetomium globosum, Coniphora cerebella, Coriolus versicolor, Lentinus tigrinus* and *Poria vaporaria.*

9. A process according to claim 7, wherein said wood contains a fungus selected from the group consisting of *Ceratocystis piceae, Ceratocystis pini, Ceratocystis coerulenceus, Chaetomium globosum, Coniphora cerebella, Coriolus versicolor, Lentinus tigrinus* and *Poria vaporaria.*

* * * * *